United States Patent [19]

Sasaki

[11] Patent Number: 5,120,304
[45] Date of Patent: Jun. 9, 1992

[54] SURGICAL FLUSHING AND ASPIRATION DEVICE

[76] Inventor: Truman Sasaki, 2108 SE. 29th, Portland, Oreg. 97214

[21] Appl. No.: 734,884

[22] Filed: Jul. 24, 1991

[51] Int. Cl.⁵ ............................................. A61M 1/00
[52] U.S. Cl. ...................... 604/35; 604/27; 604/19; 2/DIG. 7; 2/159; 2/168
[58] Field of Search ................ 604/35, 27, 19; 2/161 R, DIG. 7, 168, 163, 159, 160

[56] References Cited

U.S. PATENT DOCUMENTS

| | | | |
|---|---|---|---|
| 1,177,412 | 3/1916 | Hopkins | 2/168 X |
| 1,534,208 | 4/1925 | Gibson | 2/168 X |
| 4,766,914 | 8/1988 | Briggs | 2/159 X |

FOREIGN PATENT DOCUMENTS 0300621  1/1989  European Pat. Off. .............. 604/35

Primary Examiner—John J. Wilson
Assistant Examiner—Jeffrey A. Smith
Attorney, Agent, or Firm—Chernoff, Vilhauer, McClung & Stenzel

[57] ABSTRACT

A surgical flushing and aspiration device is disclosed that, in a preferred embodiment, comprises at least one flushing conduit for directing saline solution under positive pressure and an aspirator incorporated into a surgical glove.

6 Claims, 2 Drawing Sheets

SURGICAL FLUSHING AND ASPIRATION DEVICE

BACKGROUND OF THE INVENTION

During the course of abdominal or thoracic cavity surgery it is usually necessary to wash the cavity both to remove debris and blood from the wound or infection and to improve opportunity for visual and digital examination for purposes of diagnosis and surgical repair. The current procedure for cleansing a surgically-opened abdominal or thoracic cavity is rather primitive. A pitcher of sterile saline wash solution is poured into the cavity and manually sloshed about within the cavity to loosen debris and blood, followed by removal of the soiled solution by aspiration. This procedure is repeated until adequate cleansing is achieved; it is not uncommon that 20 to 30 liters of wash solution are required.

This conventional procedure has several disadvantages. The wash solution necessarily reaches all parts of the cavity and cannot be confined to a particular area, which may cause a localized infection to spread to other parts of the cavity. It is also time consuming because the procedure must not only be performed in three steps (pouring, sloshing, and aspiration) but usually requires several wash cycles. In addition, this method poses a risk for the surgeon because the sloshing step often results in inadvertent splashes of the wash solution along with patient's blood onto the surgeon in areas not completely protected by operating room garb, thereby exposing the surgeon to the risk of infection by contact with blood-borne bacteria and viruses.

These shortcomings of conventional surgical cavity washing are overcome by the present invention, which is summarized and described in detail below.

SUMMARY OF THE INVENTION

According to the present invention, there is provided a device for use during surgery that is capable of localized and directional surgical fluid flushing and aspiration. The device comprises fluid flushing means for delivering flushing fluid under positive pressure to an abdominal or thoracic cavity, aspiration means for removing the flushing fluid from the surgical cavity by aspiration, and means for attaching the fluid flushing means and the aspiration means to the surgeon's hand. The fluid flushing means comprises at least one flushing conduit that terminates in at least one hole for directing flushing fluid to a desired area. The aspiration means is preferably an aspiration conduit having a first end in fluid communication with a fluid scavenger and having a second end in fluid communication with a source of negative pressure. The means for attaching the fluid flushing means and the aspiration means to a hand is preferably a glove but other suitable attachment means may be used, such as a strap or a hook-and-loop fastener ("Velcro®"). When the attachment means is a glove, the glove preferably incorporates at least one conduit that terminates near a fingertip in at least one hole for directing fluid to a desired area, and an aspirator for removing fluid. When the flushing conduit terminates in several holes, a gentle spray is created when wash solution is forced therethrough under positive pressure. The aspirator comprises a fluid-conducting conduit that is under negative pressure, the conduit terminating in a fluid scavenger that is preferably convex and located in the palm area of the glove.

DETAILED DESCRIPTION OF THE INVENTION

Figure 1:
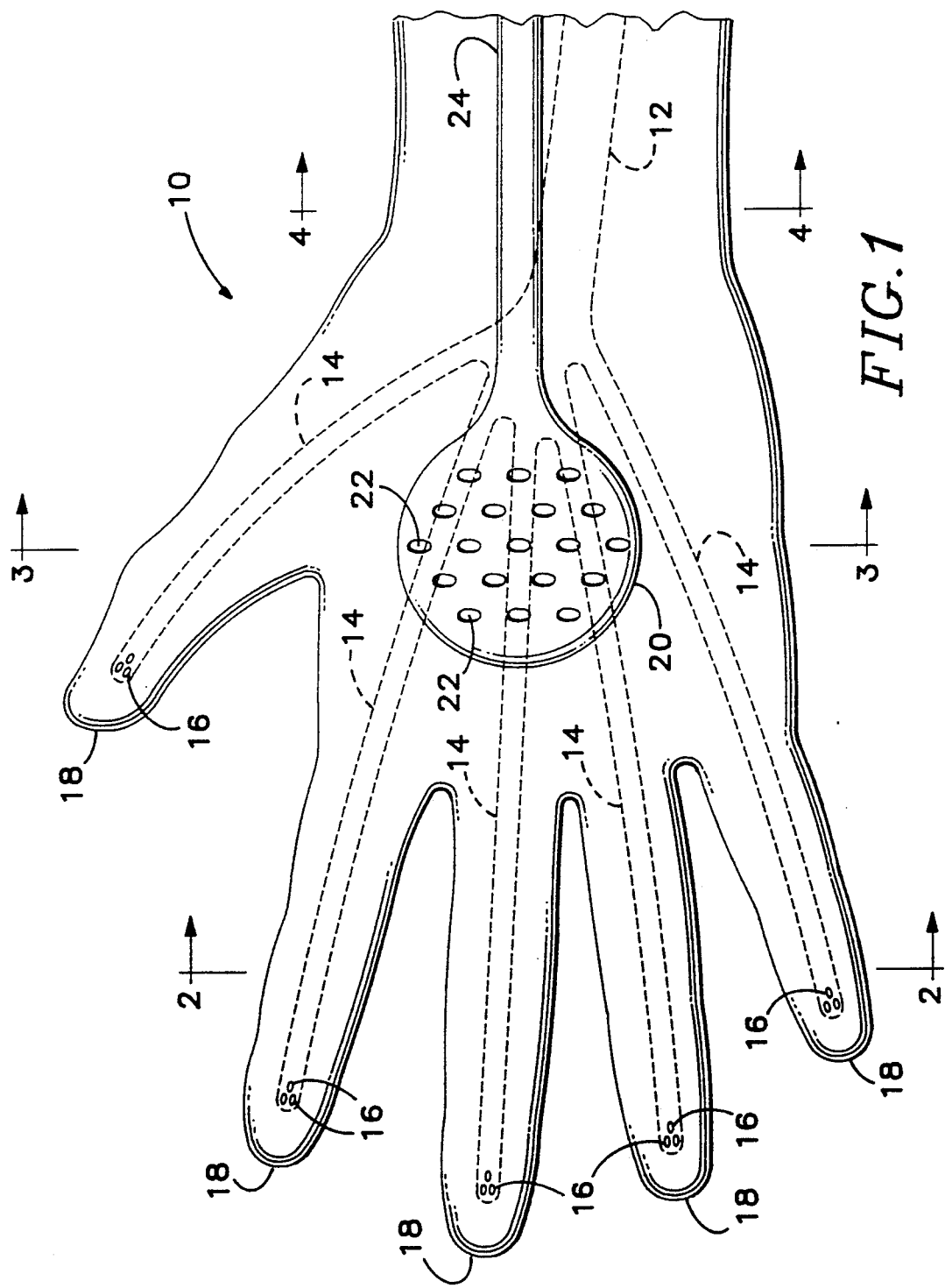
FIG. 1 is a plan view of the palm-side of a preferred embodiment of the invention.
Figure 4:
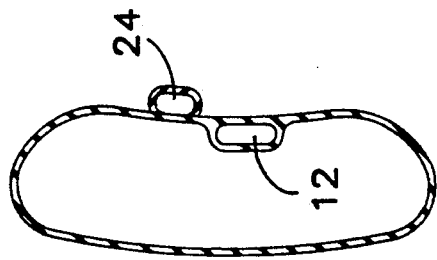
FIG. 4 is a cross-section taken through the plane 4—4 of FIG. 1.
Figure 3:
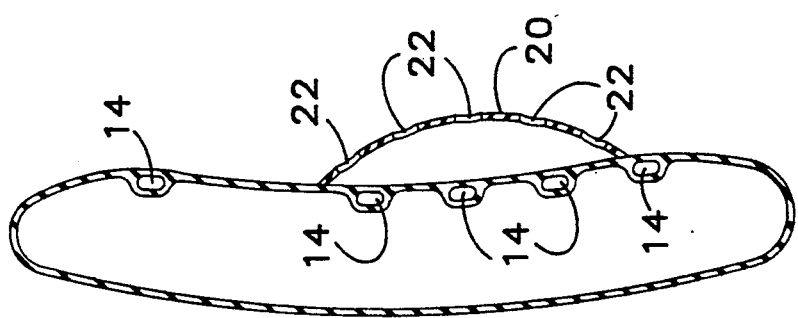
FIG. 3 is a cross-section taken through the plane 3—3 of FIG. 1.
Figure 2:
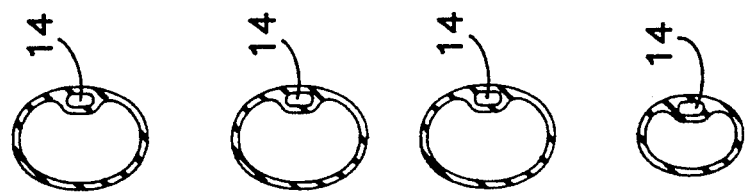
FIG. 2 is a cross-section taken through the plane 2—2 of FIG. 1.

Referring to the drawings, wherein like numerals refer to the same elements, there is shown a preferred embodiment of the invention comprising a glove 10 having a flexible flushing conduit 12 which branches into five flexible flushing conduits 14, each conduit 14 terminating in a series of spray holes 16 near the tip of a digit 18 of the glove. Although five flushing conduits 14 are shown, it will be appreciated by one of ordinary skill that the device will also have utility with more than five and with four, three, two or even a single conduit. A convex fluid scavenger 20 having a series of fluid-gathering holes 22 is located in the palm area of the glove, and is in fluid communication with another flexible return conduit 24 under negative pressure from a negative pressure source such as a vacuum pump (not shown).

In operation, saline wash fluid under positive pressure is directed through flushing conduits 12 and 14 and out spray holes 16 near the tips of digits 18 to cleanse and loosen debris in a particular area of a surgically-opened cavity while scavenger 20 aspirates wash fluid and bodily fluids such as blood from the same area through its openings 22 and to disposal through conduit 24. Because wash fluid spray can be confined to a particular desired area, possible contamination of other areas is limited. Relatively thorough cleansing action is also possible because the wash fluid is under pressure. Pressure should normally be maintained at between 1 and 2 psi, preferably 1.25–1.50 psi (corresponding to approximately 85–110 cm of water) to provide a gentle spray but may be adjusted to a higher pressure for more forceful cleansing if necessary. Digital exploration of wounds or infections during the course of washing is also possible with the present invention.

Any fluid scavenger suitable for incorporation into the present invention is acceptable as long as it is non-collapsible under the negative pressure required for aspiration. The fluid scavenger can be incorporated into the surgical glove or can be separately attached to the hand with a compatible fastening device. The negative pressure source can be capable of providing a variable pressure. Conduit 12 can be attached to any compatible conventional fluid-supplying apparatus (not shown) such as the apparatus used with cytoscopes, urologic irrigation systems and intravenous fluid supply systems. The fluid-supplying apparatus may be a bag of saline solution with gravity feed, a reservoir of saline solution connected to a pump such as a roller pump, or any other conventional apparatus. Pressure and flow controls of the flushing and aspiration means may be operated independently.

The surgical glove of the present invention is preferably fabricated from relatively thin gauge elastomeric material that is either disposable or sterilizable and may be made in various sizes and of various lengths to extend the desired distance up the arm. The flushing conduits and fluid scavenger may be incorporated into the glove detachable from the glove and reusable, preferably the latter. If detachable, conduits and scavenger can be attached to a gloved hand by any suitable means.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A surgical body cavity flushing and aspiration device comprising:
   (a) a glove having a palm and five digits, each of said digits having a tip;
   (b) at least one flushing conduit in fluid communication with a source of fluid under positive pressure, said flushing conduit terminating in at least one fluid dispensing aperture near the tip of at least one digit of said glove; and
   (c) an aspiration conduit having a first end and a second end, said first end in fluid communication with a fluid scavenger in the palm of said glove and said second end in fluid communication with a source of negative pressure.

2. The device of claim 1 wherein the source of fluid under positive pressure comprises a bag of saline solution hung from an IV stand.

3. The device of claim 1 wherein the source of fluid under positive pressure comprises a reservoir of saline solution connected to a pump.

4. The device of claim 1 wherein said source of negative pressure is a vacuum pump.

5. The device of claim 1 wherein said fluid scavenger is convex.

6. The device of claim 1 wherein said glove is disposable.

* * * * *